(12) United States Patent
Bartenbach

(10) Patent No.: US 6,869,279 B2
(45) Date of Patent: Mar. 22, 2005

(54) REACTOR FOR HIGH-TEMPERATURE REACTIONS AND USE

(75) Inventor: Bernd Bartenbach, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/806,289

(22) Filed: Mar. 23, 2004

(65) Prior Publication Data

US 2004/0191718 A1 Sep. 30, 2004

(30) Foreign Application Priority Data

Mar. 26, 2003 (DE) .......................................... 103 13 529

(51) Int. Cl.[7] .............................................. F23D 14/46
(52) U.S. Cl. ...................................... 431/353; 585/539
(58) Field of Search ................................ 431/160, 187, 431/352, 353, 242; 585/534, 539; 239/132.3

(56) References Cited

U.S. PATENT DOCUMENTS

| 4,488,866 A | * | 12/1984 | Schirmer et al. ............... 431/4 |
| 5,292,246 A | * | 3/1994 | Gateau et al. ............... 431/328 |
| 5,789,644 A | | 8/1998 | Paessler et al. |
| 5,824,834 A | * | 10/1998 | Bachtler et al. ............ 585/540 |
| 6,089,859 A | * | 7/2000 | Greiner et al. ............... 431/242 |
| 6,365,792 B1 | * | 4/2002 | Stapf et al. ................. 585/539 |

FOREIGN PATENT DOCUMENTS

| DE | 42 22815 | 1/1996 |
| DE | 199 14226 | 10/2000 |

OTHER PUBLICATIONS

Chemie Ingenieur Technik (CIT, 26 (1954) 5, p. 251.

* cited by examiner

*Primary Examiner*—Stephen Gravini
(74) *Attorney, Agent, or Firm*—Novak, Druce, DeLuca & Quigg

(57) ABSTRACT

The invention relates to a reactor (1) having a supply of a reaction mixture via channels (2) of a burner block (3) in a reaction chamber (4), a high temperature reaction having a short residence time taking place in the reaction chamber (4) and the reaction mixture then being rapidly cooled in a quench area (5). In the reactor (1), all surfaces delineating the reaction chamber (4) are formed from a fire-resistant ceramic having an alumina content of at least 80% by weight, which is stable at reaction temperature.

7 Claims, 2 Drawing Sheets

REACTOR FOR HIGH-TEMPERATURE REACTIONS AND USE

The invention relates to a reactor for high-temperature reactions, and to use of the reactor for the preparation of acetylene.

In conventional processes which proceed at high temperatures, burners having metallic walls are often employed, the walls usually being cooled by a cooling medium. A high-temperature reaction of this type is the preparation of acetylene and synthesis gas by partial oxidation of hydrocarbons, which is described, for example, in DE-A 44 22 815.

After this, the starting substances natural gas and oxygen are customarily preheated separately to up to 700° C. if possible, intensively mixed in a mixing zone and reacted after flowing through a burner block. The burner block consists of a specific number of channels in which the rate of the reaction, because of the flammable oxygen/natural gas mixture, is higher than the flame velocity in order to prevent striking through of the flame into the mixing chamber. The reaction chamber connecting to the burner block is dimensioned such that with a specific amount of substance used, the residence time of the acetylene-containing reaction gas, the "cleavage gas", is only a few milliseconds. After this time, within which the equilibriums corresponding to the temperature level of 1500 to 2000° C. cannot be established, the reaction products are if possible instantly cooled to below 300° C. using water or preferably residual oil in order that the acetylene formed does not decompose into soot and hydrogen. The decomposition reaction of the acetylene, however, cannot be completely suppressed, with the result that elemental carbon is formed, which deposits on the walls of the reaction chamber as baked on soot and coke.

In a report in Chemie Ingenieur Technik (CIT, 26 (1954) 5, p. 251), a burner lining made of chamotte is reported for a very small-scale burner for acetylene preparation according to the Sachsse-Bartholomé acetylene process. This style of construction, however, was dropped in favor of cooled metal surfaces, since on account of the low service lives of the ceramic coating, whose application threshold temperature was below the process temperature, no advantages were discernible. Constructional solutions for larger scales in the order of magnitude of 25 tonnes per day of acetylene, such as, for example, are employed today, were not available, especially with ceramic coatings under these thermal stresses.

In partially oxidative and pyrolytic processes, to which the preparation of acetylene can also be assigned, a considerable amount of soot is formed in the cleavage processes of the hydrocarbons employed. The soot preferably deposits on cold surfaces by thermophoretic processes and condensation processes, particularly during the formation phase, because of its high surface activity. This effect is particularly strong in the area of return flow zones, such as occur, for example, on the toroidal regions of the burner bores. The thickness of the layer of soot increasing in the course of the reaction leads to a successive increase in the insulating action against the cooled metal wall. On account of this insulating action, the layers of soot are subjected to thermal cracking and coking processes. By means of this, the layers of soot are converted into hard baked-on coke. On account of the hot, reactive surface, the baked-on coke accumulates further due to further soot deposition. This leads to the coke deposits having to be cleaned off mechanically. Formerly, this was carried out by hand, but today complicated poker robots are employed for this. The coke poked off by the mechanical cleaning has a coarse structure and is very hard. The coke is taken up together with the gas-phase soot in the unevaporated excess quench medium and discharged with this. On account of the coarse structure, the coke poked off has an abrasive action in the subsequent parts of the plant.

It was therefore the object of the invention to make available a reactor for a high-temperature reaction having a short residence time and having subsequent rapid cooling of the reaction mixture in a quench area, which does not have the abovementioned disadvantages.

The object is achieved by a reactor having a supply of a reaction mixture via channels of a burner block in a reaction chamber, a high-temperature reaction having a short residence time taking place in the reaction chamber and the reaction mixture then being rapidly cooled in a quench area, all the surfaces delineating the reaction chamber being formed from a fire-resistant ceramic having an alumina content of at least 80%, which is stable at reaction temperature. The invention is not restricted in principle with respect to the material for the parent substance to which the fire-resistant ceramic is to be applied. Metal materials are preferably employed for this.

High-temperature reactions are as a rule designated as reactions which take place at a temperature above 800° C., in particular, however, 1000° C.

Short residence times are designated as those which are in the millisecond range, in particular in the range from approximately 1 to 100 ms.

Rapid cooling within the meaning of the present invention is understood as meaning cooling in a time interval comparable with the residence time of the high-temperature reaction, that is a time interval in the millisecond range, preferably in the range from approximately 1 to 50 ms.

In order largely or completely to prevent soot deposition and thus coke formation, in the solution according to the invention presented here the walls of the reaction chamber are lined with a fire-resistant ceramic. Resistance of the ceramic to the temperatures of over 1650° C. occurring in the high-temperature reactions is achieved by an alumina content of at least 80%, preferably of at least 95% by weight and particularly preferably of at least 96% by weight.

The lining of the reaction chamber is carried out in a first embodiment variant by lining with masonry containing the fire-resistant ceramic in the form of stones or blocks.

In a second embodiment variant, the fire-resistant ceramic is introduced into the reaction chamber in the form of a cast or tamped mass and then compressed, dried and calcined there. In a preferred embodiment, the fire-resistant ceramic introduced into the reaction chamber as a cast or tamped mass is calcined by the high-temperature reaction.

The fire-resistant ceramic with which the reaction chamber is lined advantageously has a thickness in the range from 7 to 30 cm, preferably a thickness in the range from 8 to 10 cm.

Additionally, a back insulation of a ceramic having particularly good heat-insulating properties can be carried out.

One advantage of the reaction chamber formed according to the invention is that the lining has a thermally insulating action. For this reason, the wall of the reaction chamber no longer needs to be compulsorily cooled, which leads to a saving of cooling medium and construction outlay for the distribution of cooling medium.

A further advantage of the solution of according to the invention is that soot deposition and thus the formation of coke can be prevented even under extreme conditions, i.e. at very high temperatures and heavy soot formation, by means of sufficiently good fire-resistant insulation. By means of this, the mechanical poker device and its complicated maintenance can be saved. Moreover, owing to the saving of the mechanical poker device plant interruptions caused by poker error do not occur. Finally, the material stress due to the erosive action of the poked-off coke on the afterconnected plant parts, such as pumps, heat exchangers and pipelines, is drastically reduced.

The avoidance of the poked-off coke as described in DE-A 199 14 226, if the cleavage gas from the burner formed in the reaction is to be cooled completely or partially in a heat exchanger for waste-heat utilization, is particularly significant.

The invention is explained in greater detail below with the aid of a drawing and of a working example.

In the figures, identical reference symbols denote identical or corresponding features.

Figure 1:
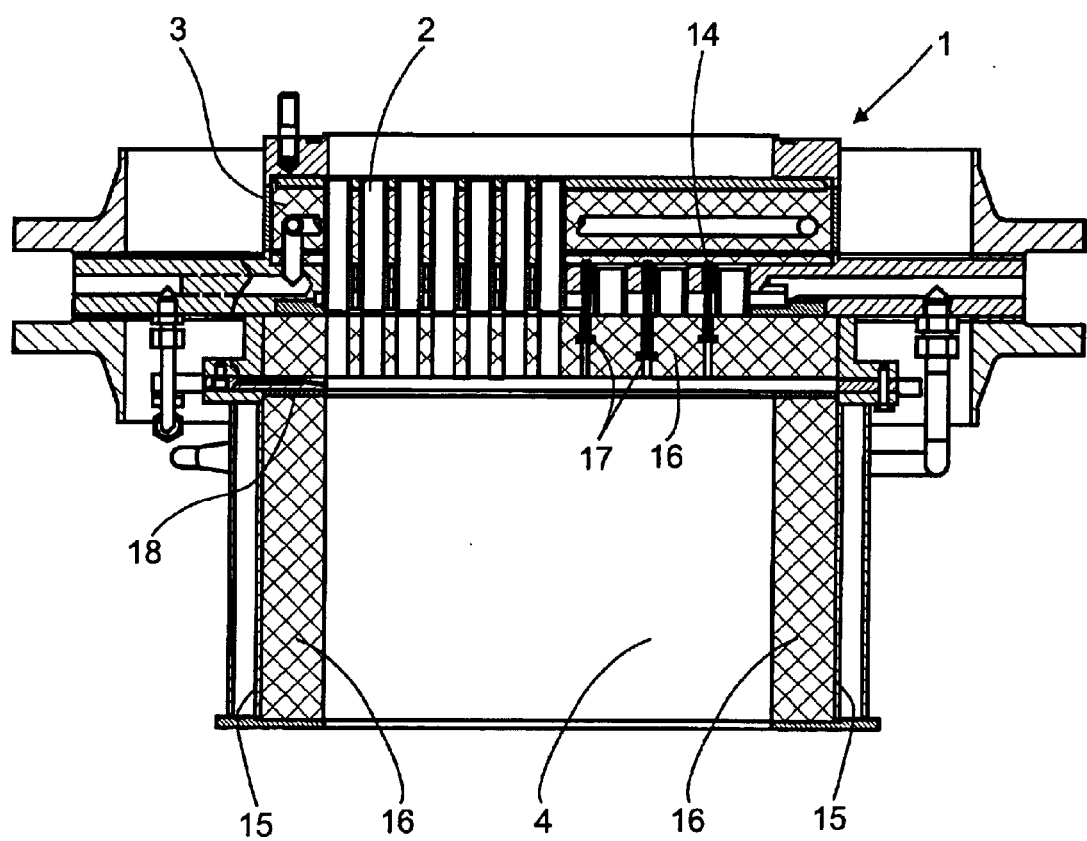
FIG. 1 shows: a section of a reactor which comprises a burner block and one embodiment of a reaction chamber designed according to the invention.

FIG. 1 shows a section of a reactor 1 designed according to the invention for acetylene preparation having a burner block 3 and reaction chamber 4. In the burner block 3, in addition to the channels 2 for the supply of the reaction mixture there are additional channels 14, via which additional oxygen or reaction auxiliaries can reach the reaction chamber 4. The reaction chamber 4 designed according to the invention shown here has side walls 15 which are lined with a fire-resistant ceramic 16. In addition to the side walls 15, the wall of the reaction chamber 4, which is delineated by the burner block 3, is also lined with fire-resistant ceramic 16. The channels 2 for the supply of the reaction mixture and the additional channels 14 for additional oxygen or reaction auxiliaries are lengthened throughout by the fire-resistant ceramic 16.

In order to prevent crack formation on account of different thermal expansion at high temperatures in the fire-resistant ceramic, anchors and expansion joints are preferably integrated into the metallic basic construction of the reactor 1.

Figure 2:
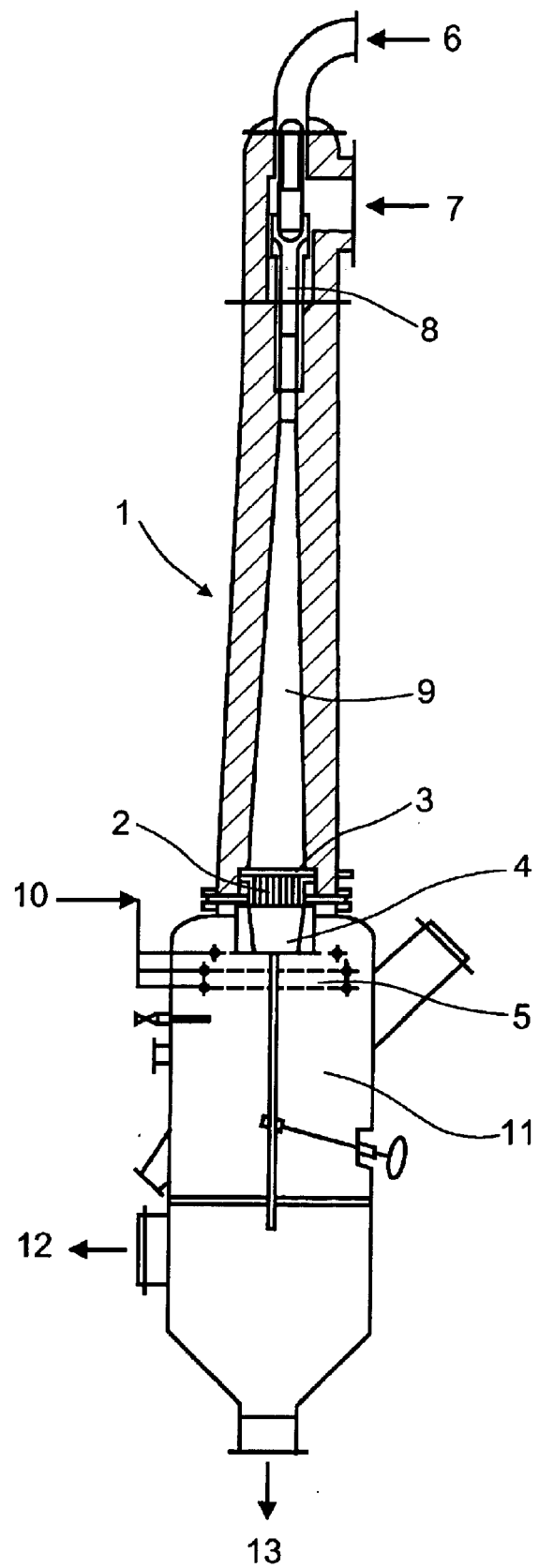
FIG. 2 shows: a reactor for acetylene preparation according to the Sachsse-Bartholomé process in accordance with the prior art.

In contrast, a reactor 1 for acetylene preparation according to the prior art is shown in FIG. 2. Oxygen or an oxygen-containing gas is supplied to the reactor via an oxygen supply 6 and a hydrocarbon or a hydrocarbon mixture is supplied to the reactor via a hydrocarbon supply 7. The oxygen or the oxygen-containing gas and the hydrocarbon or the hydrocarbon mixture are mixed in a mixing zone 8 and supplied to the burner block 3 provided with channels 2 by means of a diffuser 9. By means of the channels 2 of the burner block 3, the reaction mixture reaches a reaction chamber 4. In the reaction chamber 4, the mixture is partially oxidized to acetylene and synthesis gas in a flame. In order to avoid secondary reactions, the mixture is rapidly cooled directly following this in a quench area 5. For the rapid cooling, cooling agent is supplied to the quench area 5 via a cooling agent line 10 and directly mixed into the reaction mixture. The cooling takes place in the quench container 11 with partial evaporation of the cooling agent. Following the cooling, the cleavage gas is led off from the reactor via the cleavage gas vent 12 and the cooling agent is led off via the cooling agent outlet 13.

WORKING EXAMPLE

The efficacy of the ceramic lining with respect to soot deposition was investigated on the basis of a conventional reactor for acetylene preparation. In the reactor having a reaction chamber diameter of 533 mm as in FIG. 2 for acetylene preparation according to the Sachsse-Bartholomé process, the metallic basic construction was slightly modified and the reaction chamber was lined with a fire-resistant ceramic having a thickness of 8 cm. On operation of the reactor, it was seen that it was possible to avoid soot deposition and thus coke formation on the surfaces of the reaction chamber almost completely.

Moreover, no damage to the fire-resistant ceramic in the reaction chamber was seen. This was especially surprising insofar as the application threshold temperatures of the fire-resistant ceramics generally available and suitable for lining the reaction chamber are only slightly above the process temperatures of the partially oxidative acetylene preparation.

List of Reference Symbols 1 reactor
2 channels
3 burner block
4 reaction chamber
5 quench area
6 oxygen supply
7 hydrocarbon supply
8 mixing zone
9 diffuser
10 cooling agent line
11 quench container
12 cleavage gas vent
13 cooling agent ejection
14 addition channels
15 sidewall
16 fire-resistant ceramic
17 anchor
18 expansion joints

I claim:

1. A reactor having a supply of a reaction mixture via channels of a burner block in a reaction chamber, a high-temperature reaction having a short residence time taking place in the reaction chamber and the reaction mixture then being rapidly cooled in a quench area, wherein all surfaces delineating the reaction chamber are formed from a fire-resistant ceramic having an alumina content of at least 80% by weight, which is stable at reaction temperature.

2. A reactor as claimed in claim 1, wherein the alumina content of the fire-resistant ceramic is at least 95% by weight.

3. A reactor as claimed in claim 1, wherein the alumina content of the fire-resistant ceramic is at least 96% by weight.

4. A reactor as claimed in claim 1, wherein the fire-resistant ceramic is introduced into the reaction chamber in the form of stones or blocks or as a cast or tamped mass and then compressed, dried and calcined.

5. A reactor as claimed in claim 4, wherein the cast or tamped mass is calcined by means of the high-temperature reaction.

6. A reactor as claimed in claim 1, wherein the fire-resistant ceramic has a thickness in the range from 7 to 30 cm, preferably a thickness in the range from 8 to 10 cm.

7. A method of using the reactor as claimed in claim 1 for the preparation of acetylene by partial oxidation of hydrocarbons with oxygen.

* * * * *